United States Patent
De La Fuenta García et al.

(10) Patent No.: US 8,435,537 B2
(45) Date of Patent: May 7, 2013

(54) SYSTEM FOR THE EXPRESSION OF PEPTIDES ON THE BACTERIAL SURFACE

(75) Inventors: José De La Fuenta García, Ronda de Toledo (ES); Mario Manuel Canales García-Menocal, Ronda de Toledo (ES)

(73) Assignees: Consejo Superior de Investigaciones Científicas, Madrid (ES); Universidad de Castilla la Mancha, Ciudad Real (ES)

( * ) Notice: Subject to any disclaimer, the term of this patent is extended or adjusted under 35 U.S.C. 154(b) by 23 days.

(21) Appl. No.: 12/988,442

(22) PCT Filed: Apr. 16, 2009

(86) PCT No.: PCT/ES2009/070103
§ 371 (c)(1),
(2), (4) Date: Dec. 22, 2010

(87) PCT Pub. No.: WO2009/127766
PCT Pub. Date: Oct. 22, 2009

(65) Prior Publication Data
US 2011/0097354 A1    Apr. 28, 2011

(30) Foreign Application Priority Data
Apr. 16, 2008   (ES) .................................. 200801129

(51) Int. Cl.
*A61K 39/02*   (2006.01)
*C12N 15/70*   (2006.01)
*C07K 19/00*   (2006.01)
*A61P 37/04*   (2006.01)
*A61P 33/00*   (2006.01)

(52) U.S. Cl.
USPC ..................... 424/190.1; 435/320.1; 435/471; 435/476; 530/350; 530/402

(58) Field of Classification Search ........................ None
See application file for complete search history.

(56) References Cited

U.S. PATENT DOCUMENTS
6,979,451 B1 * 12/2005 de la Fuente et al. ...... 424/265.1

FOREIGN PATENT DOCUMENTS
WO    WO 0182957    11/2001

OTHER PUBLICATIONS

De la Fuente et al., Veterinary Parasitology, 2001, 97, 65-76.
De la Fuente et al., Veterinary Microbiology, 2003, 91, 265-283.
Garcia-Garcia et al., Vaccine, 2000, 18, 2275-2287.
International Search Report of PCT/ES2009/070103 mailed Jul. 24, 2009.
Written Opinion of PCT/ES2009/070103 mailed Jul. 24, 2009.
International Preliminary Examination Report of PCT/ES2009/070103 issued Dec. 6, 2010.

* cited by examiner

*Primary Examiner* — Robert A Zeman
(74) *Attorney, Agent, or Firm* — Merchant & Gould P.C.

(57) ABSTRACT

Expression system of peptides on the bacterial surface characterized in that membrane-binding region the conserved sequence of the MSP1a protein of *Anaplasma marginale*.

2 Claims, 5 Drawing Sheets

B

BM95 aa:  21-35          132-147           397-410
     M-SSICSDFGNEFCRNA-CDCGEWGAMNKTTRNC-LSKHVLRKLQACEH

M   K   L   L   E   M   E   H   E   N   S   M   *
    ATG AAG CTT CTC GAG ATG ... GAG CAT GAG AAT TCC ATG ... TAA
                    BM95-MSP1a fusion protein E. coli membrane

SEQUENCE LISTING

<160> NUMBER OF SEQ ID NOS: 11

<210> SEQ ID NO 1
<211> LENGTH: 529

```
<212> TYPE: PRT
<213> ORGANISM: Anaplasma marginale

<400> SEQUENCE: 1

Met Leu Ala Ala Asn Trp Arg Gln Glu Met Arg Ser Lys Val Ala Ser
1               5                   10                  15

Val Glu Tyr Ile Leu Ala Ala Arg Ala Leu Ile Ser Val Gly Val Tyr
            20                  25                  30

Ala Ala Gln Gly Glu Ile Ala Lys Ser Gln Gly Cys Ala Pro Leu Arg
        35                  40                  45

Val Ala Glu Val Glu Glu Ile Val Arg Asp Gly Leu Val Arg Ser His
    50                  55                  60

Phe His Asp Ser Gly Leu Ser Leu Gly Ser Ile Arg Leu Val Leu Met
65                  70                  75                  80

Gln Val Gly Asp Lys Leu Gly Leu Gln Leu Lys Ile Gly Glu Gly
                85                  90                  95

Tyr Ala Thr Tyr Leu Ala Gln Ala Phe Ala Asp Asn Val Val Ala
                100                 105                 110

Ala Asp Val Gln Ser Gly Gly Ala Cys Ser Ala Ser Leu Asp Ser Ala
        115                 120                 125

Ile Ala Asn Val Glu Thr Ser Trp Ser Leu His Gly Gly Leu Val Ser
    130                 135                 140

Lys Asp Phe Asp Arg Asp Thr Lys Val Glu Arg Gly Asp Leu Glu Ala
145                 150                 155                 160

Phe Val Asp Phe Met Phe Gly Gly Val Ser Tyr Asn Asp Gly Asn Ala
                165                 170                 175

Ser Ala Ala Arg Ser Val Leu Glu Thr Leu Ala Gly His Val Asp Ala
                180                 185                 190

Leu Gly Ile Ser Tyr Asn Gln Leu Asp Lys Leu Asp Ala Asp Thr Leu
        195                 200                 205

Tyr Ser Val Val Ser Phe Ser Ala Gly Ser Ala Ile Asp Arg Gly Ala
    210                 215                 220

Val Ser Asp Ala Ala Asp Lys Phe Arg Val Met Met Phe Gly Gly Ala
225                 230                 235                 240

Pro Ala Gly Gln Glu Lys Thr Ala Glu Pro Glu His Glu Ala Ala Thr
                245                 250                 255

Pro Ser Ala Ser Ser Val Pro Ser Thr Val His Gly Lys Val Val Asp
                260                 265                 270

Ala Val Asp Arg Ala Lys Glu Ala Lys Gln Ala Tyr Ala Gly Val
        275                 280                 285

Arg Lys Arg Tyr Val Ala Lys Pro Ser Asp Thr Thr Thr Gln Leu Val
    290                 295                 300

Val Ala Ile Thr Ala Leu Leu Ile Thr Ala Phe Ala Ile Cys Ala Cys
305                 310                 315                 320

Leu Glu Pro Arg Leu Ile Gly Ala Ser Gly Pro Leu Ile Trp Gly Cys
                325                 330                 335

Leu Ala Leu Val Ala Leu Leu Pro Leu Leu Gly Met Ala Val His Thr
                340                 345                 350

Ala Val Ser Ala Ser Ser Gln Lys Lys Ala Ala Gly Gly Ala Gln Arg
        355                 360                 365

Val Ala Ala Gln Glu Arg Ser Arg Glu Leu Ser Arg Ala Arg Gln Glu
    370                 375                 380

Asp Gln Gln Lys Leu His Val Pro Ala Ile Leu Thr Gly Leu Ser Val
385                 390                 395                 400
```

```
Leu Val Phe Ile Ala Ala Val Val Ala Cys Ile Ala Val Asp Ala Arg
                405                 410                 415

Arg Gly Thr Trp Gln Gly Ser Ile Cys Phe Leu Ala Ala Phe Val Leu
            420                 425                 430

Phe Ala Ile Ser Ala Ala Val Val Met Ala Thr Arg Asp Gln Ser Leu
        435                 440                 445
Ala Glu Glu Cys Asp Ser Lys Cys Ala Thr Ala Arg Thr Ala Gln Ala
    450                 455                 460

Val Pro Gly Gly Gln Gln Gln Pro Arg Ala Thr Glu Gly Val Val Ser
465                 470                 475                 480

Gly Gly Ser Gln Glu Gly Gly Ala Gly Val Pro Gly Thr Ser Val Pro
                485                 490                 495
Ser Ala Gly Ser Gly Ser Val Pro Pro Ala Thr Ile Met Val Ser Val
            500                 505                 510

Asp Pro Gln Leu Val Ala Thr Leu Gly Ala Gly Val Ala Gln Ala Ala
        515                 520                 525

Ala
```

```
<210> SEQ ID NO 2
<211> LENGTH: 1612
<212> TYPE: DNA
<213> ORGANISM: Anaplasma marginale

<400> SEQUENCE: 2
atgaagcttc tcgaggaatt ccatgttagc ggctaattgg cggcaagaga tgcgctccaa      60
ggttgcgagt gttgagtaca ttttggctgc tcgtgccctt atttctgtag ggtctatgc     120 tgctcaggga gagatcgcga aatcgcaagg gtgtgctccc ctgcgtgttg cagaagtcga     180
agaaatcgtg agggatggcc ttgtacgcag ccactttcat gatagtggcc tttcactagg     240
ctccatacga ctcgtgctta tgcaggttgg ggataagttg gggctacaag gtttgaagat     300
tggcgaaggg tacgccacct atctcgcgca agcgtttgct gacaacgtgg tggttgcggc     360
tgatgttcaa agtggtggtg cgtgctctgc cagccttgac agcgcgatcg caaacgttga     420
gacgtcgtgg tccctgcacg gcggcctggt aagcaaagat tttgaccgtg ataccaaagt     480
agaaaggggc gaccttgagg cttttgtcga cttcatgttt ggcggtgtgt cgtacaatga     540
tgggaacgcg tctgcggcta ggagcgtatt ggaaacgctt gccgggcacg tcgatgcact     600
tggtatatcg tacaatcagc tggataagct tgatgctgac actttgtata gtgtcgtatc     660
gtttagtgcc ggttccgcaa tagacagagg tgcggttagc gatgcggctg acaagttccg     720
tgtgatgatg tttggtggtg ctcctgcggg gcaagagaaa actgccgaac ctgagcatga     780
ggctgcgacc ccgtcagcta gtagcgttcc gtcaactgtg catggtaagg tcgttgatgc     840
agttgaccgt gcaaaagaag cggctaagca ggcctatgca ggcgtgcgta agcggtatgt     900
ggcgaagcct tcggacacta ctacacagct tgttgtagct atcacggcgc tgcttatcac     960
ggcgtttgct atctgtgcgt gtttggaacc taggcttata ggggcgtccg gtccgctgat    1020
ttggggctgc ctggcactag tagcactgct gccattactt ggtatggctg tgcatacggc    1080
agtgagtgct tcgagtcaaa agaaggctgc cggtggtgcg caacgggttg ctgctcagga    1140
gaggtctagg gaattgtccc gtgcgagaca ggaagatcag cagaagttgc atgttcccgc    1200
gatactgacc gggttgagcg tgcttgtgtt tattgctgcc gtcgtggctt gtattgctgt    1260
tgacgcgagg cgcgggacgt ggcagggcag catatgtttc ctagccgcat ttgtgttgtt    1320
tgcgatcagt gccgctgttg taatggcaac acgtgaccaa tcgttggcag aagagtgtga    1380
```

```
tagcaagtgt gctacagctc gtacggctca agctgtaccc ggtggccagc agcagccgcg    1440
tgctaccgag ggcgttgtta gcggtggcag ccaagaaggc ggggctggtg ttcccggaac    1500
ttccgtgccg tcagccgggt ctgggtccgt acctcctgct accattatgg tcagtgtgga    1560
tccacaactt gttgctactt tgggagcagg tgtggcgcag gcggcggcgt aa             1612
```

```
<210> SEQ ID NO 3
<211> LENGTH: 46
<212> TYPE: PRT
<213> ORGANISM: Artificial Sequence
<220> FEATURE:
<223> OTHER INFORMATION: Chimeric protein BM95

<400> SEQUENCE: 3
```

| Met | Ser | Ser | Ile | Cys | Ser | Asp | Phe | Gly | Asn | Glu | Phe | Cys | Arg | Asn | Ala |
|---|---|---|---|---|---|---|---|---|---|---|---|---|---|---|---|
| 1 | | | | 5 | | | | | 10 | | | | | 15 | |

| Cys | Asp | Cys | Gly | Glu | Trp | Gly | Ala | Met | Asn | Lys | Thr | Thr | Arg | Asn | Cys |
|---|---|---|---|---|---|---|---|---|---|---|---|---|---|---|---|
| | | | 20 | | | | | 25 | | | | | 30 | | |

| Leu | Ser | Lys | His | Val | Leu | Arg | Lys | Leu | Gln | Ala | Cys | Glu | His |
|---|---|---|---|---|---|---|---|---|---|---|---|---|---|
| | | 35 | | | | | 40 | | | | | 45 | |

```
<210> SEQ ID NO 4
<211> LENGTH: 569
<212> TYPE: PRT
<213> ORGANISM: Rhipicephalus microplus

<400> SEQUENCE: 4
```

| Met | Arg | Gly | Ile | Ala | Leu | Phe | Val | Ala | Ala | Val | Ser | Leu | Ile | Val | Glu |
|---|---|---|---|---|---|---|---|---|---|---|---|---|---|---|---|
| 1 | | | | 5 | | | | | 10 | | | | | 15 | |

| Gly | Thr | Ala | Glu | Ser | Ser | Ile | Cys | Ser | Asp | Phe | Gly | Asn | Glu | Phe | Cys |
|---|---|---|---|---|---|---|---|---|---|---|---|---|---|---|---|
| | | | 20 | | | | | 25 | | | | | 30 | | |

| Arg | Asn | Ala | Glu | Cys | Glu | Val | Val | Pro | Gly | Ala | Glu | Asp | Asp | Phe | Val |
|---|---|---|---|---|---|---|---|---|---|---|---|---|---|---|---|
| | | 35 | | | | | 40 | | | | | 45 | | | |

| Cys | Lys | Cys | Pro | Arg | Asp | Asn | Met | Tyr | Phe | Asn | Ala | Ala | Glu | Lys | Gln |
|---|---|---|---|---|---|---|---|---|---|---|---|---|---|---|---|
| | 50 | | | | | 55 | | | | | 60 | | | | |

| Cys | Glu | Tyr | Lys | Asp | Thr | Cys | Lys | Thr | Arg | Glu | Cys | Ser | Tyr | Gly | Arg |
|---|---|---|---|---|---|---|---|---|---|---|---|---|---|---|---|
| 65 | | | | | 70 | | | | | 75 | | | | | 80 |

| Cys | Val | Glu | Ser | Asn | Pro | Ser | Lys | Gly | Ser | Cys | Val | Cys | Glu | Arg | Ser |
|---|---|---|---|---|---|---|---|---|---|---|---|---|---|---|---|
| | | | | 85 | | | | | 90 | | | | | 95 | |

| Asp | Asp | Leu | Thr | Leu | Gln | Cys | Lys | Ile | Lys | Asn | Asp | Tyr | Ala | Thr | Asp |
|---|---|---|---|---|---|---|---|---|---|---|---|---|---|---|---|
| | | | 100 | | | | | 105 | | | | | 110 | | |

| Cys | Arg | Asn | Arg | Gly | Gly | Thr | Ala | Lys | Leu | Arg | Thr | Asp | Gly | Phe | Ile |
|---|---|---|---|---|---|---|---|---|---|---|---|---|---|---|---|
| | | 115 | | | | | 120 | | | | | 125 | | | |

| Gly | Ala | Thr | Cys | Asp | Cys | Gly | Glu | Trp | Gly | Ala | Met | Asn | Lys | Thr | Thr |
|---|---|---|---|---|---|---|---|---|---|---|---|---|---|---|---|
| | 130 | | | | | 135 | | | | | 140 | | | | |

| Arg | Asn | Cys | Val | Pro | Thr | Thr | Cys | Leu | Arg | Pro | Asp | Leu | Thr | Cys | Lys |
|---|---|---|---|---|---|---|---|---|---|---|---|---|---|---|---|
| 145 | | | | | 150 | | | | | 155 | | | | | 160 |

| Asp | Leu | Cys | Glu | Lys | Asn | Leu | Leu | Gln | Arg | Asp | Ser | Arg | Cys | Cys | Gln |
|---|---|---|---|---|---|---|---|---|---|---|---|---|---|---|---|
| | | | | 165 | | | | | 170 | | | | | 175 | |

| Gly | Trp | Asn | Thr | Ala | Asn | Cys | Ser | Ala | Ala | Pro | Pro | Ala | Asp | Ser | Tyr |
|---|---|---|---|---|---|---|---|---|---|---|---|---|---|---|---|
| | | | 180 | | | | | 185 | | | | | 190 | | |

| Cys | Ser | Pro | Gly | Ser | Pro | Lys | Gly | Pro | Asp | Gly | Gln | Cys | Lys | Asn | Ala |
|---|---|---|---|---|---|---|---|---|---|---|---|---|---|---|---|
| | | 195 | | | | | 200 | | | | | 205 | | | |

| Cys | Arg | Thr | Lys | Glu | Ala | Gly | Phe | Val | Cys | Lys | His | Gly | Cys | Arg | Ser |
|---|---|---|---|---|---|---|---|---|---|---|---|---|---|---|---|
| | 210 | | | | | 215 | | | | | 220 | | | | |

| Thr | Asp | Lys | Ala | Tyr | Glu | Cys | Thr | Cys | Pro | Ser | Gly | Ser | Thr | Val | Ala |
|---|---|---|---|---|---|---|---|---|---|---|---|---|---|---|---|
| 225 | | | | | 230 | | | | | 235 | | | | | 240 |

```
Glu Asp Gly Ile Thr Cys Lys Ser Ile Ser Tyr Thr Val Ser Cys Thr
                245                 250                 255
Val Glu Gln Lys Gln Thr Cys Arg Pro Thr Glu Asp Cys Arg Val Gln
            260                 265                 270
Lys Gly Thr Val Leu Cys Glu Cys Pro Trp Asn Gln His Leu Val Gly
        275                 280                 285
Asp Thr Cys Ile Ser Asp Cys Val Asp Lys Lys Cys His Glu Glu Phe
    290                 295                 300
Met Asp Cys Gly Val Tyr Met Asn Arg Gln Ser Cys Tyr Cys Pro Trp
305                 310                 315                 320
Lys Ser Arg Lys Pro Gly Pro Asn Val Asn Ile Asn Glu Arg Leu Leu
                325                 330                 335
Asn Glu Tyr Tyr Tyr Thr Val Ser Phe Thr Pro Asn Ile Ser Phe Asp
            340                 345                 350
Ser Asp His Cys Lys Arg Tyr Glu Asp Arg Val Leu Gly Ala Ile Arg
        355                 360                 365
Thr Ser Ile Gly Lys Glu Val Phe Lys Val Glu Ile Leu Asn Cys Thr
    370                 375                 380
Gln Asp Ile Lys Ala Arg Leu Ile Ala Glu Lys Pro Leu Ser Lys Tyr
385                 390                 395                 400
Val Leu Arg Lys Leu Gln Ala Cys Glu His Pro Ile Gly Glu Trp Cys
                405                 410                 415
Met Met Tyr Pro Lys Leu Leu Ile Lys Lys Asn Ser Ala Thr Glu Ile
            420                 425                 430
Glu Glu Glu Asn Leu Cys Asp Ser Leu Leu Lys Asn Gly Glu Ala Ala
        435                 440                 445
Tyr Lys Gly Gln Asn Lys Cys Val Lys Val Asp Asn Leu Phe Trp Phe
    450                 455                 460
Gln Cys Ala Asp Gly Tyr Thr Thr Thr Tyr Glu Met Thr Arg Gly Arg
465                 470                 475                 480
Leu Arg Arg Ser Val Cys Lys Ala Gly Val Ser Cys Asn Glu Asn Glu
                485                 490                 495
Gln Leu Glu Cys Ala Asn Lys Gly Gln Ile Cys Val Tyr Glu Asn Gly
            500                 505                 510
Lys Ala Asn Cys Gln Cys Pro Pro Asp Thr Lys Pro Gly Glu Ile Gly
        515                 520                 525
Cys Ile Glu Arg Thr Thr Cys Asn Pro Lys Glu Ile Gln Glu Cys Gln
    530                 535                 540
Asp Lys Lys Leu Glu Cys Val Tyr Lys Asn His Lys Ala Glu Cys Lys
545                 550                 555                 560
Cys Pro Asp Asp His Glu Cys Ser Arg
                565

<210> SEQ ID NO 5
<211> LENGTH: 83
<212> TYPE: DNA
<213> ORGANISM: Artificial Sequence
<220> FEATURE:
<223> OTHER INFORMATION: Oligonucleotide Bmtin5

<400> SEQUENCE: 5
atgtcatcca tttgctctga cttcgggaac gagttctgtc gcaacgcttg tgactgtggt      60
gaatggggtg cgatgaacaa gac                                             83

<210> SEQ ID NO 6
<211> LENGTH: 85
```

```
<212> TYPE: DNA
<213> ORGANISM: Artificial Sequence
<220> FEATURE:
<223> OTHER INFORMATION: Oligonucleotide Bmtin3

<400> SEQUENCE: 6
atgctcgcat gcttgtagtt tcctgagcac gtgttttgac agacagttcc gtgtggtctt      60
gttcatcgca ccccattcac cacag                                            85

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide B5

<400> SEQUENCE: 7
ccctcgagat gtcatccatt tgctctgact tcg                                   33

<210> SEQ ID NO 8
<211> LENGTH: 38
<212> TYPE: DNA
<213> ORGANISM: Artificial Sequence
<220> FEATURE:
<223> OTHER INFORMATION: Oligonucleotide B3

<400> SEQUENCE: 8
ccggaattct catgctcgca tgcttgtagt ttcctgag                              38

<210> SEQ ID NO 9
<211> LENGTH: 6950
<212> TYPE: DNA
<213> ORGANISM: Artificial Sequence
<220> FEATURE:
<223> OTHER INFORMATION: Plasmid pAF0R1

<400> SEQUENCE: 9
catcataacg gttctggcaa atattctgaa atgagctgtt gacaattaat catcggctcg      60
tataatgtgt ggaattgtga gcggataaca atttcacaca ggagatatca tatgaaaaag     120
acagctatcg cgattgcagt ggcactggct ggtttcgcta ccgttgcgca agcttatgaa     180
gcttctcgag gaattccatg ttagcggcta attggcggca agagatgcgc tccaaggttg     240
cgagtgttga gtacattttg gctgctcgtg cccttatttc tgtaggggtc tatgctgctc     300
agggagagat cgcgaaatcg caagggtgtg ctcccctgcg tgttcagaa gtcgaagaaa      360 tcgtgaggga tggccttgta cgcagccact ttcatgatag tggcctttca ctaggctcca     420
tacgactcgt gcttatgcag gttgggata agttgggct acaaggtttg aagattggcg       480
aagggtacgc cacctatctc gcgcaagcgt ttgctgacaa cgtggtggtt gcggctgatg     540
ttcaaagtgg tggtgcgtgc tctgccagcc ttgacagcgc gatcgcaaac gttgagacgt     600
cgtggtccct gcacggcggc ctggtaagca aagattttga ccgtgatacc aaagtagaaa     660
ggggcgacct tgaggctttt gtcgacttca tgtttggcgg tgtgtcgtac aatgatggga     720
acgcgtctgc ggctaggagc gtattggaaa cgcttgccgg gcacgtcgat gcacttggta     780
tatcgtacaa tcagctggat aagcttgatg ctgacacttt gtatagtgtc gtatcgttta     840
gtgccggttc cgcaatagac agaggtgcgg ttagcgatgc ggctgacaag ttccgtgtga     900
tgatgtttgg tggtgctcct gcggggcaag agaaaactgc cgaacctgag catgaggctg     960
cgaccccgtc agctagtagc gttccgtcaa ctgtgcatgg taaggtcgtt gatgcagttg    1020
accgtgcaaa agaagcggct aagcaggcct atgcaggcgt gcgtaagcgg tatgtggcga    1080
```

```
agccttcgga cactactaca cagcttgttg tagctatcac ggcgctgctt atcacggcgt   1140
ttgctatctg tgcgtgtttg gaacctaggc ttatagggc  gtccggtccg ctgatttggg   1200
gctgcctggc actagtagca ctgctgccat tacttggtat ggctgtgcat acggcagtga   1260
gtgcttcgag tcaaaagaag gctgccggtg gtgcgcaacg ggttgctgct caggagaggt   1320
ctagggaatt gtcccgtgcg agacaggaag atcagcagaa gttgcatgtt cccgcgatac   1380
tgaccgggtt gagcgtgctt gtgtttattg ctgccgtcgt ggcttgtatt gctgttgacg   1440
cgaggcgcgg gacgtggcag ggcagcatat gttccctagc cgcatttgtg ttgtttgcga   1500
tcagtgccgc tgttgtaatg gcaacacgtg accaatcgtt ggcagaagag tgtgatagca   1560
agtgtgctac agctcgtacg gctcaagctg tacccggtgg ccagcagcag ccgcgtgcta   1620
ccgagggcgt tgttagcggt ggcagccaag aaggcggggc tggtgttccc ggaacttccg   1680
tgccgtcagc cgggtctggg tccgtacctc ctgctaccat tatggtcagt gtggatccac   1740
aacttgttgc tactttggga gcaggtgtgg cgcaggcggc ggcgtaatga agatcgatct   1800
ctcgatcgag tgagagaaga ttttcagcct gatacagatt aaatcagaag cggtctgata   1860
aaacagaatt tgcctggcgg cagtagcgcg gtggtcccac ctgaccccat gccgaactca   1920
gaagtgaaac gccgtagcgc cgatggtagt gtggggtctc cccatgcgag agtagggaac   1980
tgccaggcat caaataaaac gaaaggctca gtcgaaagac tgggcctttc gttttatctg   2040
ttgtttgtcg gtgaacgctc tcctgagtag acaaatccg  ccgggagcgg atttgaacgt   2100
tgcgaagcaa cggcccggag ggtggcgggc aggacgcccg ccataaactg ccaggcatca   2160
aattaagcag aaggccatcc tgacggatgg cctttttgcg tttctacaaa ctcttttgtt   2220
tatttttcta aatacattca aatatgtatc cgctcatgag acaataaccc tgataaatgc   2280
ttcaataata ttgaaaaagg aagagtatga gtattcaaca tttccgtgtc gcccttattc   2340
ccttttttgc ggcattttgc cttcctgttt ttgctcaccc agaaacgctg gtgaaagtaa   2400
aagatgctga agatcagttg ggtgcacgag tgggttacat cgaactggat ctcaacagcg   2460
gtaagatcct tgagagtttt cgccccgaag aacgttttcc aatgatgagc acttttaaag   2520
ttctgctatg tggcgcggta ttatcccgtg ttgacgccgg gcaagagcaa ctcggtcgcc   2580
gcatacacta ttctcagaat gacttggttg agtactcacc agtcacagaa aagcatctta   2640
cggatggcat gacagtaaga gaattatgca gtgctgccat aaccatgagt gataacactg   2700
cggccaactt acttctgaca acgatcggag gaccgaagga gctaaccgct tttttgcaca   2760
acatggggga tcatgtaact cgccatgatc gttgggaacc ggagctgaat gaagccatac   2820
caaacgacga gcgtgacacc acgatgcctg tagcaatggc aacaacgttg cgcaaactat   2880
taactggcga actacttact ctagcttccc ggcaacaatt aatagactgg atggaggcgg   2940
ataaagttgc aggaccactt ctgcgctcgg cccttccggc tggctggttt attgctgata   3000
aatctggagc cggtgagcgt gggtctcgcg gtatcattgc agcactgggg ccagatggta   3060
agccctcccg tatcgtagtt atctacacga cggggagtca ggcaactatg gatgaacgaa   3120
atagacagat cgctgagata ggtgcctcac tgattaagca ttggtaactg tcagaccaag   3180
tttactcata tactttag   attgatttaa aacttcattt ttaatttaaa aggatctagg   3240
tgaagatcct ttttgataat ctcatgacca aaatccctta acgtgagttt cgttccact   3300 gagcgtcaga ccccgtagaa aagatcaaag gatcttcttg agatcctttt tttctgcgcg   3360
taatctgctg cttgcaaaca aaaaaaccac cgctaccagc ggtggtttgt ttgccggatc   3420
aagagctacc aactcttttt ccgaaggtaa ctggcttcag cagagcgcag ataccaaata   3480
```

```
ctgtccttct agtgtagccg tagttaggcc accacttcaa gaactctgta gcaccgccta    3540
catacctcgc tctgctaatc ctgttaccag tggctgctgc cagtggcgat aagtcgtgtc    3600
ttaccgggtt ggactcaaga cgatagttac cggataaggc gcagcggtcg ggctgaacgg    3660
ggggttcgtg cacacagccc agcttggagc gaacgaccta caccgaactg agatacctac    3720
agcgtgagca ttgagaaagc gccacgcttc ccgaagggag aaaggcggac aggtatccgg    3780
taagcggcag ggtcggaaca ggagagcgca cgagggagct ccaggggga aacgcctggt    3840 atctttatag tcctgtcggg tttcgccacc tctgacttga gcgtcgattt ttgtgatgct    3900 cgtcagggg gcggagccta tggaaaaacg ccagcaacgc ggccttttta cggttcctgg    3960
ccttttgctg gccttttgct cacatgttct ttcctgcgtt atccctgat tctgtggata    4020 accgtattac cgcctttgag tgagctgata ccgctcgccg cagccgaacg accgagcgca    4080
gcgagtcagt gagcgaggaa gcggaagagc gcctgatgcg gtattttctc cttacgcatc    4140
tgtgcggtat ttcacaccgc agatcctgac gcgccctgta gcggcgcatt aagcgcggcg    4200
ggtgtggtgg ttacgcgcag cgtgaccgct acacttgcca gcgccctagc gcccgctcct    4260
ttcgctttct tcccttcctt tctcgccacg ttcgccggct ttccccgtca gctctaaat    4320 cgggggctcc ctttagggtt ccgatttagt gctttacggc acctcgaccc caaaaaactt    4380
gattagggtg atggttcacg tagtgggcca tcgccctgat agacggtttt tcgccctttg    4440
acgttggagt ccacgttctt taatagtgga ctcttgttcc aaactggaac aacactcaac    4500
cctatctcgg tctattcttt tgatttataa gggattttgc cgatttcggc ctattggtta    4560
aaaaatgagc tgatttaaca aaaatttaac gcgaatttta acaaaatatt aacgtttaca    4620
ggatctggtg cactctcagt acaatctgct ctgatgccgc atagttaagc cagtatacac    4680
tccgctatcg ctacgtgact gctcgacctg cagcaattca acgccatcaa aataattcg    4740 cgtctggcct tcctgtagcc agctttcatc aacattaaat gtgagcgagt aacaacccgt    4800
cggattctcc gtgggaacaa acggcggatt gaccgtaatg ggataggtta cgttggtgta    4860
gatgggcgca tcgtaaccgt gcatctgcca gtttgagggg acgacgacag tatcggcctc    4920
aggaagatcg cactccagcc agctttccgg caccgcttct ggtgccggaa accaggcaaa    4980
gcgccattcg ccattcaggc tgcgcaactg ttgggaaggg cgatcggtgc gggcctcttc    5040
gctattacgc cagctggcga aaggggggatg tgctgcaagg cgattaagtt gggtaacgcc    5100
agggttttcc cagtcacgac gttgtaaaac gacggccagt gaatccgtaa tcatggtcat    5160
agctgtttcc tgtgtgaaat tgttatccgc tcacaattcc acacaacata cgagccggaa    5220
gcataaagtg taaagcctgg ggtgcctaat gagtgagcta actcacatta attgcgttgc    5280
gctcactgcc cgctttccag tcgggaaacc tgtcgtgcca gctgcattaa tgaatcggcc    5340
aacgcgcggg gagaggcggt ttgcgtattg ggcgccaggg tggttttct tttcaccagt    5400 gagacgggca acagctgatt gcccttcacc gcctggccct gagagagttg cagcaagcgg    5460
tccacgctgg tttgccccag caggcgaaaa tcctgtttga tggtggttga cggcgggata    5520
taacatgagc tgtcttcggt atcgtcgtat cccactaccg agatatccgc accaacgcgc    5580
agcccggact cggtaatggc gcgcattgcg cccagcgcca tctgatcgtt ggcaaccagc    5640
atcgcagtgg gaacgatgcc ctcattcagc atttgcatgg tttgttgaaa accggacatg    5700
gcactccagt cgccttcccg ttcgctatc ggctgaattt gattgcgagt gagatattta    5760
tgccagccag ccagacgcag acgcgccgag acagaactta atgggcccgc taacagcgcg    5820
atttgctggt gacccaatgc gaccagatgc tccacgccca gtcgcgtacc gtcttcatgg    5880
```

```
gagaaaataa tactgttgat gggtgtctgg tcagagacat caagaaataa cgccggaaca      5940
ttagtgcagg cagcttccac agcaatggca tcctggtcat ccagcggata gttaatgatc      6000
agcccactga cgcgttgcgc gagaagattg tgcaccgccg ctttacaggc ttcgacgccg      6060
cttcgttcta ccatcgacac caccacgctg gcacccagtt gatcggcgcg agatttaatc      6120
gccgcgacaa tttgcgacgg cgcgtgcagg gccagactgg aggtggcaac gccaatcagc      6180
aacgactgtt tgcccgccag ttgttgtgcc acgcggttgg gaatgtaatt cagctccgcc      6240
atcgccgctt ccacttttc ccgcgttttc gcagaaacgt ggctggcctg gttcaccacg       6300
cgggaaacgg tctgataaga gacaccggca tactctgcga catcgtataa cgttactggt      6360
ttcacattca ccaccctgaa ttgactctct tccgggcgct atcatgccat accgcgaaag      6420
gttttgcacc attccatggt gtcgaattgc tgcaggtcga ggggtcatg gctgcgcccc       6480 gacacccgcc aacacccgct gacgcgcccct gacgggcttg tctgctcccg gcatccgctt     6540
acagacaagc tgtgaccgtc tccgggagct gcatgtgtca gaggttttca ccgtcatcac      6600
cgaaacgcgc gaggcagcaa ggagatggcg cccaacagtc ccccggccac gggcctgcca     6660
ccatacccac gccgaaacaa cgctcatga gcccgaagtg gcgagcccga tcttccccat      6720
cggtgatgtc ggcgatatag gcgccagcaa ccgcacctgt ggcgccggtg atgccggcca     6780
cgatgcgtcc ggcgtagagg atccggagct tatcgactgc acggtgcacc aatgcttctg      6840
gcgtcaggca gccatcggaa gctgtggtat ggctgtgcag gtcgtaaatc actgcataat      6900
tcgtgtcgct caaggcgcac tcccgttctg gataatgttt tttgcgccga               6950
```

<210> SEQ ID NO 10
<211> LENGTH: 7090
<212> TYPE: DNA
<213> ORGANISM: Artificial Sequence
<220> FEATURE:
<223> OTHER INFORMATION: Plasmid pMBXAF3

<400> SEQUENCE: 10

```
catcataacg gttctggcaa atattctgaa atgagctgtt gacaattaat catcggctcg        60
tataatgtgt ggaattgtga gcggataaca atttcacaca ggagatatca tatgaaaaag      120
acagctatcg cgattgcagt ggcactggct ggtttcgcta ccgttgcgca agcttatgaa       180
gcttctcgag atgtcatcca tttgctctga cttcgggaac gagttctgtc gcaacgcttg      240
tgactgtggt gaatggggtg cgatgaacaa gaccacacgg aactgtctgt caaaacacgt      300
gctcaggaaa ctacaagcat gcgagcatga gaattccatg ttagcggcta attggcggca     360
agagatgcgc tccaaggttg cgagtgttga gtacattttg gctgctcgtg cccttatttc       420
tgtaggggtc tatgctgctc agggagagat cgcgaaatcg caagggtgtg ctcccctgcg      480
tgttgcagaa gtcgaagaaa tcgtgaggga tggccttgta cgcagccact ttcatgatag      540
tggcctttca ctaggctcca tacgactcgt gcttatgcag gttggggata agttggggct      600
acaaggtttg aagattggcg aagggtacgc cacctatctc gcgcaagcgt ttgctgacaa      660
cgtggtggtt gcggctgatg ttcaaagtgg tggtgcgtgc tctgccagcc ttgacagcgc       720
gatcgcaaac gttgagacgt cgtggtccct gcacggcggc ctggtaagca aagattttga      780
ccgtgatacc aaagtagaaa ggggcgacct tgaggctttt gtcgacttca tgtttggcgg      840
tgtgtcgtac aatgatggga acgcgtctgc ggctaggagc gtattggaaa cgcttgccgg      900
gcacgtcgat gcacttggta tatcgtacaa tcagctggat aagcttgatg ctgacacttt      960
gtatagtgtc gtatcgttta gtgccggttc cgcaatagac agaggtgcgg ttagcgatgc     1020
```

```
ggctgacaag ttccgtgtga tgatgtttgg tggtgctcct gcggggcaag agaaaactgc    1080
cgaacctgag catgaggctg cgaccccgtc agctagtagc gttccgtcaa ctgtgcatgg    1140
taaggtcgtt gatgcagttg accgtgcaaa agaagcggct aagcaggcct atgcaggcgt    1200
gcgtaagcgg tatgtggcga agccttcgga cactactaca cagcttgttg tagctatcac    1260
ggcgctgctt atcacggcgt ttgctatctg tgcgtgtttg gaacctaggc ttataggggc    1320
gtccggtccg ctgatttggg gctgcctggc actagtagca ctgctgccat tacttggtat    1380
ggctgtgcat acggcagtga gtgcttcgag tcaaaagaag gctgccggtg gtgcgcaacg    1440
ggttgctgct caggagaggt ctagggaatt gtcccgtgcg agacaggaag atcagcagaa    1500
gttgcatgtt cccgcgatac tgaccgggtt gagcgtgctt tgtgtttattg ctgccgtcgt    1560 ggcttgtatt gctgttgacg cgaggcgcgg gacgtggcag gcagcatat gtttcctagc    1620 cgcatttgtg ttgtttgcga tcagtgccgc tgttgtaatg gcaacacgtg accaatcgtt    1680
ggcagaagag tgtgatagca agtgtgctac agctcgtacg gctcaagctg tacccggtgg    1740
ccagcagcag ccgcgtgcta ccgagggcgt tgttagcggt ggcagccaag aaggcggggc    1800
tggtgttccc ggaacttccg tgccgtcagc cgggtctggg tccgtacctc ctgctaccat    1860
tatggtcagt gtggatccac aacttgttgc tactttggga gcaggtgtgg cgcaggcggc    1920
ggcgtaatga agatcgatct ctcgatcgag tgagagaaga ttttcagcct gatacagatt    1980
aaatcagaag cggtctgata aacagaatt tgcctggcgg cagtagcgcg gtggtcccac    2040
ctgaccccat gccgaactca gaagtgaaac gccgtagcgc cgatggtagt gtggggtctc    2100
cccatgcgag agtagggaac tgccaggcat caaataaaac gaaaggctca gtcgaaagac    2160
tgggcctttc gttttatctg ttgtttgtcg gtgaacgctc tcctgagtag acaaatccg    2220 ccgggagcgg atttgaacgt tgcgaagcaa cggcccggag ggtggcgggc aggacgcccg    2280
ccataaactg ccaggcatca aattaagcag aaggccatcc tgacggatgg cctttttgcg    2340
tttctacaaa ctcttttgtt tattttttcta aatacattca aatatgtatc cgctcatgag    2400
acaataaccc tgataaatgc ttcaataata ttgaaaaagg aagagtatga gtattcaaca    2460
tttccgtgtc gcccttattc ccttttttgc ggcattttgc cttcctgttt ttgctcaccc    2520
agaaacgctg gtgaaagtaa agatgctgaa gatcagttg ggtgcacgag tgggttacat    2580
cgaactggat ctcaacagcg gtaagatcct tgagagtttt cgccccgaag aacgttttcc    2640
aatgatgagc acttttaaag ttctgctatg tggcgcggta ttatcccgtg ttgacgccgg    2700
gcaagagcaa ctcggtcgcc gcatacacta ttctcagaat gacttggttg agtactcacc    2760
agtcacagaa aagcatctta cggatggcat gacagtaaga gaattatgca gtgctgccat    2820
aaccatgagt gataacactg cggccaactt acttctgaca acgatcggag gaccgaagga    2880
gctaaccgct tttttgcaca acatggggga tcatgtaact cgccatgatc gttgggaacc    2940
ggagctgaat gaagccatac caaacgacga gcgtgacacc acgatgcctg tagcaatggc    3000
aacaacgttg cgcaaactat taactggcga actacttact ctagcttccc ggcaacaatt    3060
aatagactgg atggaggcgg ataaagttgc aggaccactt ctgcgctcgg cccttccggc    3120
tggctggttt attgctgata atctggagc cggtgagcgt gggtctcgcg gtatcattgc    3180
agcactgggg ccagatggta agccctcccg tatcgtagtt atctacacga cggggagtca    3240
ggcaactatg gatgaacgaa atagacagat cgctgagata ggtgcctcac tgattaagca    3300
ttggtaactg tcagaccaag tttactcata tatactttag attgatttaa aacttcattt    3360
ttaatttaaa aggatctagg tgaagatcct ttttgataat ctcatgacca aaatccctta    3420
```

```
acgtgagttt tcgttccact gagcgtcaga ccccgtagaa aagatcaaag gatcttcttg   3480
agatccttt  tttctgcgcg taatctgctg cttgcaaaca aaaaaaccac cgctaccagc   3540
ggtggtttgt tgccggatc  aagagctacc aactctttt  ccgaaggtaa ctggcttcag   3600
cagagcgcag ataccaaata ctgtccttct agtgtagccg tagttaggcc accacttcaa   3660
gaactctgta gcaccgccta catacctcgc tctgctaatc ctgttaccag tggctgctgc   3720
cagtggcgat aagtcgtgtc ttaccgggtt ggactcaaga cgatagttac cggataaggc   3780
gcagcggtcg ggctgaacgg ggggttcgtg cacacagccc agcttggagc gaacgaccta   3840
caccgaactg agatacctac agcgtgagca ttgagaaagc gccacgcttc ccgaagggag   3900
aaaggcggac aggtatccgg taagcggcag gtcggaaca  ggagagcgca cgagggagct   3960
tccagggga  aacgcctggt atctttatag tcctgtcggg tttcgccacc tctgacttga   4020
gcgtcgattt tgtgatgct  cgtcaggggg gcggagccta tggaaaaacg ccagcaacgc   4080
ggccttttta cggttcctgg ccttttgctg ccttttgct  cacatgttct ttcctgcgtt   4140
atccctgat  tctgtggata accgtattac cgcctttgag tgagctgata ccgctcgccg   4200
cagccgaacg accgagcgca gcgagtcagt gagcgaggaa gcggaagagc gcctgatgcg   4260
gtatttctc  cttacgcatc tgtgcggtat tcacaccgc  agatcctgac gcgccctgta   4320
gcggcgcatt aagcgcggcg ggtgtggtgg ttacgcgcag cgtgaccgct acacttgcca   4380
gcgccctagc gcccgctcct ttcgctttct tcccttcctt tctcgccacg ttcgccggct   4440
ttccccgtca gctctaaat  cggggctcc  ctttagggtt ccgatttagt gctttacggc   4500
acctcgaccc caaaaaactt gattagggtg atggttcacg tagtgggcca tcgccctgat   4560
agacggtttt tcgccctttg acgttggagt ccacgttctt aatagtgga  ctcttgttcc   4620
aaactggaac aacactcaac cctatctcgg tctattcttt tgatttataa gggattttgc   4680
cgatttcggc ctattggtta aaaatgagc  tgatttaaca aaaatttaac gcgaatttta   4740
acaaaatatt aacgtttaca ggatctggtg cactctcagt acaatctgct ctgatgccgc   4800
atagttaagc cagtatacac tccgctatcg ctacgtgact gctcgacctg cagcaattca   4860
acgccatcaa aaataattcg cgtctggcct tcctgtagcc agctttcatc aacattaaat   4920
gtgagcgagt aacaacccgt cggattctcc gtgggaacaa acggcggatt gaccgtaatg   4980
ggataggtta cgttggtgta gatgggcgca tcgtaaccgt gcatctgcca gtttgagggg   5040
acgacgacag tatcggcctc aggaagatcg cactccagcc agctttccgg caccgcttct   5100
ggtgccggaa accaggcaaa gcgccattcg ccattcaggc tgcgcaactg ttgggaaggg   5160
cgatcggtgc gggcctcttc gctattacgc cagctggcga aaggggatg  tgctgcaagg   5220
cgattaagtt gggtaacgcc agggttttcc cagtcacgac gttgtaaaac gacggccagt   5280
gaatccgtaa tcatggtcat agctgttttcc tgtgtgaaat tgttatccgc tcacaattcc   5340
acacaacata cgagccggaa gcataaagtg taaagcctgg ggtgcctaat gagtgagcta   5400
actcacatta attgcgttgc gctcactgcc cgctttccag tcgggaaacc tgtcgtgcca   5460
gctgcattaa tgaatcggcc aacgcgcggg gagaggcggt ttgcgtattg ggcgccaggg   5520
tggtttttct tttcaccagt gagacgggca acagctgatt gcccttcacc gcctggccct   5580
gagagagttg cagcaagcgg tccacgctgg tttgccccag caggcgaaaa tcctgtttga   5640
tggtggttga cggcgggata taacatgagc tgtcttcggt atcgtcgtat cccactaccg   5700
agatatccgc accaacgcgc agcccggact cggtaatggc gcgcattgcg cccagcgcca   5760
tctgatcgtt ggcaaccagc atcgcagtgg gaacgatgcc ctcattcagc atttgcatgg   5820
```

```
tttgttgaaa accggacatg gcactccagt cgccttcccg ttccgctatc ggctgaattt    5880
gattgcgagt gagatattta tgccagccag ccagacgcag acgcgccgag acagaactta    5940
atgggcccgc taacagcgcg atttgctggt gacccaatgc gaccagatgc tccacgccca    6000
gtcgcgtacc gtcttcatgg agaaaataa tactgttgat gggtgtctgg tcagagacat     6060
caagaaataa cgccggaaca ttagtgcagg cagcttccac agcaatggca tcctggtcat    6120
ccagcggata gttaatgatc agcccactga cgcgttgcgc gagaagattg tgcaccgccg    6180
ctttacaggc ttcgacgccg cttcgttcta ccatcgacac caccacgctg cacccagtt     6240
gatcggcgcg agatttaatc gccgcgacaa tttgcgacgg cgcgtgcagg ccagactgg     6300
aggtggcaac gccaatcagc aacgactgtt gcccgccag ttgttgtgcc acgcggttgg     6360
gaatgtaatt cagctccgcc atcgccgctt ccacttttc ccgcgttttc gcagaaacgt     6420
ggctggcctg gttcaccacg cgggaaacgg tctgataaga gacaccggca tactctgcga    6480
catcgtataa cgttactggt ttcacattca ccaccctgaa ttgactctct tccgggcgct    6540
atcatgccat accgcgaaag gttttgcacc attccatggt gtcgaattgc tgcaggtcga    6600
gggggtcatg gctgcgcccc gacacccgcc aacacccgct gacgcgccct gacgggcttg    6660
tctgctcccg gcatccgctt acagacaagc tgtgaccgtc tccgggagct gcatgtgtca    6720
gaggttttca ccgtcatcac cgaaacgcgc gaggcagcaa ggagatggcg cccaacagtc    6780
ccccggccac gggcctgcca ccatacccac gccgaaacaa gcgctcatga gcccgaagtg    6840
gcgagcccga tcttcccat cggtgatgtc ggcgatatag cgccagcaa ccgcacctgt      6900
ggcgccggtg atgccggcca cgatgcgtcc ggcgtagagg atccggagct tatcgactgc    6960
acggtgcacc aatgcttctg gcgtcaggca gccatcggaa gctgtggtat ggctgtgcag    7020
gtcgtaaatc actgcataat tcgtgtcgct caaggcgcac tcccgttctg gataatgttt    7080
tttgcgccga                                                            7090
```

<210> SEQ ID NO 11
<211> LENGTH: 583
<212> TYPE: PRT
<213> ORGANISM: Artificial Sequence
<220> FEATURE:
<223> OTHER INFORMATION: Fused protein BM95-MSP1a

<400> SEQUENCE: 11

Met Lys Leu Leu Glu Met Ser Ser Ile Cys Ser Asp Phe Gly Asn Glu
1               5                   10                  15

Phe Cys Arg Asn Ala Cys Asp Cys Gly Glu Trp Gly Ala Met Asn Lys
            20                  25                  30

Thr Thr Arg Asn Cys Leu Ser Lys His Val Leu Arg Lys Leu Gln Ala
        35                  40                  45

Cys Glu His Glu Asn Ser Met Leu Ala Ala Asn Trp Arg Gln Glu Met
    50                  55                  60

Arg Ser Lys Val Ala Ser Val Glu Tyr Ile Leu Ala Ala Arg Ala Leu
65                  70                  75                  80

Ile Ser Val Gly Val Tyr Ala Ala Gln Gly Glu Ile Ala Lys Ser Gln
                85                  90                  95

Gly Cys Ala Pro Leu Arg Val Ala Glu Val Glu Ile Val Arg Asp
            100                 105                 110

Gly Leu Val Arg Ser His Phe His Asp Ser Gly Leu Ser Leu Gly Ser
        115                 120                 125

Ile Arg Leu Val Leu Met Gln Val Gly Asp Lys Leu Gly Leu Gln Gly

```
                    130                 135                 140
Leu Lys Ile Gly Glu Gly Tyr Ala Thr Tyr Leu Ala Gln Ala Phe Ala
145                 150                 155                 160

Asp Asn Val Val Ala Ala Asp Val Gln Ser Gly Gly Ala Cys Ser
                165                 170                 175

Ala Ser Leu Asp Ser Ala Ile Ala Asn Val Glu Thr Ser Trp Ser Leu
                180                 185                 190

His Gly Gly Leu Val Ser Lys Asp Phe Asp Arg Asp Thr Lys Val Glu
                195                 200                 205

Arg Gly Asp Leu Glu Ala Phe Val Asp Phe Met Phe Gly Gly Val Ser
210                 215                 220

Tyr Asn Asp Gly Asn Ala Ser Ala Ala Arg Ser Val Leu Glu Thr Leu
225                 230                 235                 240

Ala Gly His Val Asp Ala Leu Gly Ile Ser Tyr Asn Gln Leu Asp Lys
                245                 250                 255

Leu Asp Ala Asp Thr Leu Tyr Ser Val Val Ser Phe Ser Ala Gly Ser
                260                 265                 270

Ala Ile Asp Arg Gly Ala Val Ser Asp Ala Ala Asp Lys Phe Arg Val
                275                 280                 285

Met Met Phe Gly Gly Ala Pro Ala Gly Gln Glu Lys Thr Ala Glu Pro
                290                 295                 300

Glu His Glu Ala Ala Thr Pro Ser Ala Ser Ser Val Pro Ser Thr Val
305                 310                 315                 320

His Gly Lys Val Val Asp Ala Val Asp Arg Ala Lys Glu Ala Ala Lys
                325                 330                 335

Gln Ala Tyr Ala Gly Val Arg Lys Arg Tyr Val Ala Lys Pro Ser Asp
                340                 345                 350

Thr Thr Thr Gln Leu Val Val Ala Ile Thr Ala Leu Leu Ile Thr Ala
                355                 360                 365

Phe Ala Ile Cys Ala Cys Leu Glu Pro Arg Leu Ile Gly Ala Ser Gly
                370                 375                 380

Pro Leu Ile Trp Gly Cys Leu Ala Leu Val Ala Leu Leu Pro Leu Leu
385                 390                 395                 400

Gly Met Ala Val His Thr Ala Val Ser Ala Ser Ser Gln Lys Lys Ala
                405                 410                 415

Ala Gly Gly Ala Gln Arg Val Ala Ala Gln Glu Arg Ser Arg Glu Leu
                420                 425                 430

Ser Arg Ala Arg Gln Glu Asp Gln Gln Lys Leu His Val Pro Ala Ile
                435                 440                 445

Leu Thr Gly Leu Ser Val Leu Val Phe Ile Ala Ala Val Val Ala Cys
                450                 455                 460

Ile Ala Val Asp Ala Arg Arg Gly Thr Trp Gln Gly Ser Ile Cys Phe
465                 470                 475                 480

Leu Ala Ala Phe Val Leu Phe Ala Ile Ser Ala Val Val Met Ala
                485                 490                 495

Thr Arg Asp Gln Ser Leu Ala Glu Glu Cys Asp Ser Lys Cys Ala Thr
                500                 505                 510

Ala Arg Thr Ala Gln Ala Val Pro Gly Gly Gln Gln Pro Arg Ala
                515                 520                 525

Thr Glu Gly Val Val Ser Gly Gly Ser Gln Glu Gly Gly Ala Gly Val
                530                 535                 540

Pro Gly Thr Ser Val Pro Ser Ala Gly Ser Gly Ser Val Pro Pro Ala
545                 550                 555                 560
```

-continued

```
Thr Ile Met Val Ser Val Asp Pro Gln Leu Val Ala Thr Leu Gly Ala
                565                 570                 575
Gly Val Ala Gln Ala Ala Ala
            580
```

SYSTEM FOR THE EXPRESSION OF PEPTIDES ON THE BACTERIAL SURFACE

This application is a National Stage Application of PCT/ES2009/070103, filed 16 Apr. 2009, which claims benefit of Serial No. P200801129, filed 16 Apr. 2008 in Spain and which applications are incorporated herein by reference. To the extent appropriate, a claim of priority is made to each of the above disclosed applications.

The present invention is within the biotechnological, biochemistry and chemical-pharmaceutical sectors. The object of the invention is a method to expose recombinant polypeptides expressed on the bacterial surface. It can be applied in basic or applied research in molecular biology, biochemistry, biotechnology or in the production of recombinant proteins for various purposes.

PRIOR ART

The technology that allows the expression of a protein or peptide, binding it to the cell surface, for example, of microorganisms such as bacteria or yeasts, has numerous applications depending on the type of protein expressed on the surface, and therefore, an enormous industrial interest.

Therefore, the interest in exposing proteins or peptides on the surface of live bacteria has been increasing in areas of biochemical, molecular biology and biotechnology research. The exposure of heterologous proteins using membrane-binding motifs of proteins such as LamB, OmpA, PhoE, TratT, OprF, OprI, FHA, INP, fimbriae, and AIDA-I and the self-exposure system have already served to express antigens and enzymes. The protein to be exposed must be fused with the binding protein or proteins, which are often proteins from the cell surface or fragments thereof ("carrier proteins"), by an N-terminal fusion, a C-terminal fusion or a sandwich fusion. The characteristics of the binding protein, the exposed protein and the method of fusion affects the efficiency of the expression on the surface of proteins.

The surface expression of proteins has multiple applications including:
a. the development of live vaccines, on exposing heterologous epitopes of human guests or pathogenic bacterial cells attenuated to elicit the response of antigen-specific antibodies,
b. the search for libraries of peptides by sequential bonding and elusion or, more efficiently, by fluorescence-activated cell-sorting (FACS),
c. production of antibodies expressing surface antigens to obtain polyclonal antibodies in animals,
d. bioabsorbents to eliminate harmful chemicals and heavy metals,
e. biocatalysis by enzyme immobilisation,
f. development of biosensors by binding of enzymes, receptors or other components sensitive to signals for diagnosis, industrial or environmental purposes,
g. detection of changes in amino acids in target peptides after random mutagenesis.

*Anaplasma marginale* (Rickettsiales: Anaplasmataceae) is a pathogen transmitted by ticks that causes bovine anaplasmosis, a disease which causes considerable financial losses in livestock production. The MSP1a protein (Major Surface Protein 1a) is one of the five main surface proteins known of *A. marginale* and is involved in the adhesion of the pathogen to the hosts and in the interactions of the pathogen with the ticks. This protein has evolved under a positive selective pressure and its molecular size is different between strains of different geographical areas. The variations are due to the fact that a sequence of 23 to 31 consecutive amino acids is repeated a different number of times, at the N-terminal end, of the region that the protein exposes on the bacterial surface.

It has been demonstrated that MSP1a allows the bacteria to adhere to bovine erythrocytes and to tick cells. The adhesion domain of the protein has been precisely identified in the variable region of the N-terminal end containing the repeated peptides. MSP1a is also involved in the transmission of *A. marginale* by the ticks of the *Dermacentor* spp. genus and the repeated peptides of the N-terminal end, which have B cell epitopes, could be involved in the protective response of livestock to infections by *A. marginale*.

The tick *Boophilus microplus* (recently reclassified as *Rhipicephalus microplus*) considerably affects cattle of the planet's tropical and subtropical regions. The BM86 antigen, encoded by the Bm86 gene, is a glycoprotein isolated from the intestinal cells of *R. microplus* which have been used in a vaccine against infestations by these ticks. A gene homologous to Bm86, Bm95, was also isolated from a strain of *R. microplus* (Strain A) and its encoding protein, BM95, showed protective capacity against a greater number of ticks from different geographical regions. The first experiments performed by the inventors, characterised the presence of immunogenic peptides in the BM86 protein. It was later demonstrated that these peptides were responsible for inducing the protective response of the livestock vaccinated against infestations by ticks.

The present invention demonstrates that a recombinant protein, composed of the immunogenic peptides of BM95 fused with the N-terminal region of the MSP1a protein of *A. marginale*, is exposed on the surface of live *E. coli* cells and is recognised by anti-BM86 and anti-MSP1a antibodies. This system provides a novel model of exposure of heterologous proteins on live bacteria cells and also suggests the possibility of using recombinant bacteria in immunisation studies of cattle against livestock infestations.

For the success of the expression of the protein on the cell surface, the binding motif is the most important. The core of this technology consists of the choice of a motif capable of expressing a protein or heterologous peptide on the cell surface effectively. A suitable binding protein must have the following four requirements: it must have a transporter that allows the premature fusion protein to pass through the internal membrane; it must have a strong binding structure to sustain the fusion proteins on the cell surface; it must be compatible with the external sequences on being inserted or fused, and finally, they must be resistant to attack by the proteases present in the periplasmic medium or space.

The expression systems known to date have drawbacks, the fundamental one being the limitation for the membrane presentation of polypeptides with different number and composition of amino acids, one of the main aspects the object of the present invention tackles.

DESCRIPTION OF THE INVENTION

The present invention relates to the use of a portion of the MSP1a protein of *A. marginale* to direct the exposure of other peptides on the cell surface, by their N-terminal fusion with this protein. Bearing in mind the natural size range of the peptides repeated in the N-terminal region of MSP1a (28-289 amino acids) and the examples of embodiment stated in this specification, one advantage of using the MSP1a protein instead of other protein membrane-binding motifs to expose peptides on the cell surface is the possibility of exposing polypeptides of different sizes and composition of amino acids.

In accordance with a first aspect of the present invention, an expression system of peptides on the bacterial surface is provided, hereinafter the expression system of the invention, characterised in that it comprises a bacterial membrane-binding region and the exposed peptide, where any of the following sequences is used as a bacterial membrane-binding region:

a. Peptide which comprises the amino acid sequence SEQ ID NO: 1.
b. An amino acid sequence with an identity of at least 99%, 98%, 95%, 90%, or 80% with SEQ ID NO: 1.

Hereinafter, "amino acid sequence of the invention" is understood to be the sequence of amino acids of the portion of the MSP1a protein of *Anaplasma marginale*, or a protein with an identity of at least 80%, and more preferably 90%, 95%, 98%, and even more preferably 99% with said portion of the MSP1a protein, included in SEQ ID NO: 1. And "exposed peptide" shall be understood as the sequence of amino acids one wants to express on the bacterial surface, and which is bound or fused to the amino acid sequence of the invention.

The term "peptide", as used in the present invention, includes both the full length protein and the shorter sequences of polypeptides and peptides.

The term "polynucleotide" or "polynucleotide sequence", as used here, relates to a polymeric form of nucleotides of any length, either ribonucleotides or deoxyribonucleotides. This term only relates to the primary structure of the molecule. Thus, this term includes double or single strand DNA, and double or single strand RNA. It also includes all known types of modifications (markers known in the state of the art, methylation, finishes, substitution of one or more of the natural nucleotides with an analogue, internucleotide modifications such as, for example, those with uncharged bonds (for example, methyl phosphonates, phosphorous triesters, phosphorous amidates, carbamates, etc.) and with charged bonds (for example, phosphorous thioates, phosphorous thioates, etc.), those containing hanging halves such as, for example, proteins (including, for example, nucleases, toxins, antibodies, signal peptides, poly-L-lysine, etc.), those with intercalating agents (for example, acridine, psoralen, etc.), those containing chelating agents (for example, metals, radioactive metals, boron, oxidative metals, etc.), those containing alkylating agents, those with modified bonds (for example, alpha-anomeric nucleic acids, etc.), as well as unmodified forms of the polynucleotide. "Polynucleotide sequence of the invention" is understood as the polynucleotide sequence which encodes for the amino acid sequence of the invention, and which may be, for example, SEQ ID NO: 2.

In a preferred embodiment of this aspect of the invention, the bacteria on whose surface the peptide of interest is expressed is *Escherichia coli* (*E. coli*). *Escherichia coli* (*E. coli*), gram negative bacteria, facultative and non-sporulated anaerobia, with a genome of approximately 4.6 kb, is perhaps the prokaryotic organism most widely studied by man. Some strains of this bacterium are enormously versatile in the laboratory, tolerating genetic manipulation very well and even losing their pathogenic capacity, for which reason it is used as "model organism" for the study of structures, genetic and physiological mechanisms and their extrapolation to a large number of microorganisms, including the eukaryotic cell.

In another embodiment of this aspect of the invention, the exposed peptide is not MSP1.

In accordance with another aspect of the present invention, a genetic construction is provided, hereinafter genetic construction of the invention, which directs the in vitro or intracellular transcription of the polynucleotide sequences of the expression system of the invention, and comprises at least one of the following types of sequences:

a. sequence of nucleotides, preferably double strand, which encodes the amino acid sequence of the expression system of the invention, or
b. nucleic acid molecules whose complementary strand hybridises with the polynucleotide sequence of a),
c. nucleic acid molecules whose sequence differs from a) and/or b) due to the degeneration of the genetic code,
d. sequence of nucleotides of a), b), or c), preferably double strand, corresponding to a gene expression vector or system, operationally bound to, at least, a promoter which directs the transcription of said sequence of nucleotides of interest, and with other sequences necessary or appropriate for the transcription and its suitable regulation in time and place, for example, start and end signals, cut sites, polyadenylation signal, origin of replication, enhancers, silencers, etc.

This method includes the cloning and expression vectors which comprise the nucleic acid molecules of the expression system of the invention. Said expression vectors include suitable control sequences, such as, for example, translation control elements (such as start and stop codes) and transcription control elements (for example, promoter-operator regions, binding regions). The vectors in accordance with the invention may include plasmids and virus (comprising bacteriophages and eukaryotic viruses), in accordance with processes well known and documented in the state of the art, and they can be expressed in a variety of different expression systems, also well known and documented in the state of the art. The suitable viral vectors include baculovirus and also adenovirus and vaccination virus. Many other viral and non-viral vectors are described and known in the state of the art.

A variety of techniques are also known that can be used to introduce these vectors in prokaryotic or eukaryotic cells for their expression. Suitable transformation or transfection techniques are also described in the literature.

The transformed or transfected eukaryotic or prokaryotic host cells containing a nucleic acid molecule in accordance with the invention, as previously defined, also form part of this aspect of the invention.

Since the nucleotide and amino acid sequences of the expression system of the invention are similar in terms of their evolution, it can be expected that the overall identity of the genomes on an amino acid level, obtained from different strains populations and/or individuals of *Anaplasma marginale*, and more specifically on an amino acid sequence level included in SEQ ID NO: 1, is 80% or more, and more preferably 90% or more and more preferably 95, 98 or 99% or more. The correspondence between the amino acid sequence of SEQ ID NO: 1 and the sequence belonging to another individual or organism can be determined by methods known in the art.

Multiples of these expression vectors or systems may be obtained by conventional methods known by persons skilled in the art (Sambrook et al., 1989) and form part of the present invention.

In a particular embodiment of this aspect of the invention, the genetic construction of the invention is included in a plasmid.

The peptides exposed can also be prepared by expression in a host cell containing a recombinant DNA molecule which comprises a sequence of nucleotides that transcribes the peptides, operationally bound to a control sequence of the expression, or a recombinant DNA cloning vector or vehicle which contains said molecule of recombinant DNA. Alternatively, the peptides may be expressed by direct injection of a single DNA molecule in a host cell. Another aspect of the invention provides a method to prepare the expression system of the invention, which comprises the following steps:
  a. Introducing the genetic construction of the invention, or a plasmid of the invention, in a host cell.
  b. Incubating the host cell according to a. in a suitable reaction medium.

In a particular embodiment of this aspect of the invention, the host cell is *E. coli*.

Another aspect of the invention provides a recombinant peptide, hereinafter recombinant peptide of the invention, obtainable or obtained from the expression system of the invention. In a preferred embodiment of this aspect of the invention, the recombinant peptide is obtained from the lysis of the host cell which comprises the expression system of the invention, and its subsequent purification.

The exposed peptides may be, for example, but without being limited to, antigenic peptides that act as vaccines to protect against future infections or to enhance the immune response against infection in already infected subjects or animals.

As previously mentioned, a possible advantage of using the MSP1a protein over the aforementioned about using protein membrane-binding motifs to expose proteins on the bacterial surface, if we bear in mind the natural size range of the repeated peptides of MSP1a (28 to 289 amino acids) and the results reported in this specification, is the possibility of expressing and exposing on the bacterial surface, peptides of different sizes and compositions.

The peptides expressed may have protective antigen sequences. The expression "protective antigen", as used in the present invention, defines those antigens capable of generating a protective immune response (immunogenic) of the host, i.e. a response of the host, that leads to the generation of immune effector molecules, antibodies or cells that sterilise or reduce the reproduction rate of the invader organism or damage it, inhibit it or kill it, thus "protecting" the host from the clinical or subclinical disease and from a loss of productivity. Said protective immune response may be commonly manifested by the generation of antibodies that are capable of inhibiting the metabolic function of the invading organism, leading to an impediment of its normal growth, lack of reproduction and/or death.

The polypeptide thus expressed can be a fusion polypeptide which comprises a portion which deploys the immunogenicity, and an additional peptide encoded by the DNA of the recombinant molecule fused thereto, and which is translated to the amino acid sequence of SEQ ID NO: 1.

The exposed peptides can, therefore, be used as immunogen. These immunogens may also be used as vaccines in animals, and more particularly in mammals, including humans, to produce a response in the production of antibodies in animals. Therefore, an immunologically effective quantity of at least one of these recombinant peptides is administered to a mammal including humans.

An alternative method of vaccines production is the use of molecular biology techniques to produce a fusion protein that contains one or several of the amino acid sequence of the present invention and a highly immunogenic peptide or protein, against a certain infection or infestation.

Another aspect of the invention relates to the expression system of the invention, the genetic construction of the invention, the plasmid of the invention or the recombinant peptide of the invention, for their use as drug. In a preferred embodiment of this aspect of the invention, the drug is a vaccine.

In another preferred embodiment of the invention, the fusion protein or the recombinant peptide is BM95-MSP1.

The peptide BM95 could be used to induce a protective immune response against infestations by *Rhipicephalus microplus* ticks, in cattle.

The expression system, object of this preferred embodiment of the invention, is made up of a plasmid vector with replication system for *E. coli* and selection marker via antibiotic resistance, preferably ampicillin. A promoter efficient in *E. Coli* is inserted in this vector such as derivatives of lactose (lac) and tryptophan (tryp) operon. The encoding gene for a MSP1a mutant is inserted against the promoter which lacks six amino acids preceding the repeated peptides and the actual repeated peptides, but which contains the ten amino acids previous to the first transmembrane region of the protein starting with an ATG start codon. Finally, the XhoI and EcoRI restriction sites are inserted for the cloning of polypeptides in phase with MSP1a for the expression exposed on the *E. coli*. membrane (FIG. 1). The system consists of a novel expression system of exposed polypeptides on live *E. coli* cells for various uses.

The term "identity", as used in this specification, makes reference to the proportion of identical amino acids between two amino acid sequences compared.

A "vector" is a replicon whereto another polynucleotide segment has been bound to perform the replication and/or expression of the bound segment.

A "replicon" is any genetic element that behaves as an autonomous unit of polynucleotide replication within a cell; i.e. capable of replicating under its own control.

"Control sequence" relates to sequences of polynucleotides that are necessary for carrying out the expression of encoding sequences whereto they are linked. The nature of said control sequences differs depending on the host organism; in prokaryotes, said control sequences generally include a promoter, a ribosomal binding region, and end signals; in eukaryotes, generally, said control sequences include promoters, end signals, intensifiers and, on occasions, silencers. It is intended that the term "control sequences" includes, at least, all components whose presence is necessary for the expression and may also include additional components whose presence is advantageous.

"Operationally bound" relates to a juxtaposition wherein the components thus described have a relation which allows them to work in the intended manner. An "operationally bound" control sequence is linked so that the expression of the encoding sequence is achieved in conditions compatible with the control sequences.

An "open reading frame" (ORF) is a region of a sequence of polynucleotides which encodes a polypeptide; this region may represent a portion of encoding sequence or a complete encoding sequence.

An "encoding sequence" is a sequence of polynucleotides that is transcribed to mRNA and/or is translated to a polypeptide when it is under control of appropriate regulatory sequences. The limits of the encoding sequence are determined by a translation start codon at end 5' and a translation end codon at end 3'. An encoding sequence may include, but is not limited to mRNA, cDNA, and sequences of recombinant polynucleotides.

As used in this specification, the term "transfection" relates to the introduction or transference of an exogenous nucleic acid molecule in an eukaryote cell, including, but not being limited to, a molecule of ribonucleic or deoxyribonucleic acid (for example, bare RNA or DNA).

The term "plasmid" relates to a circular fragment of double-stranded DNA, which is found inside almost all bacteria, and which act and replicate independently to the bacterial chromosomal DNA and can be transferred from some bacteria to others. They are used as vectors in genetic manipulation.

In the context of the present invention, the term "vaccine" relates to an antigenic preparation used to establish the response of the immune system to a disease. They are preparations of antigens which, once inside the organism, cause immune system response, by the production of antibodies, and generate immune memory producing permanent or transitory immunity.

The term "drug", as used in this specification, refers to any substance used for the prevention, diagnosis, relief, treatment or cure of diseases in man and animals. In the context of the present invention it also relates to the expression system of the invention, the genetic construction of the invention, the plasmid of the invention or the recombinant peptide of the invention, capable of generating an immune response to a given organism, which is causing said disease in man or in animals. It, therefore, includes what is known as vaccine, as previously defined in this specification.

The term "antigen" in this specification relates to a cell surface molecule (generally, a protein or polysaccharide), which may induce antibody formation. There are many types of different molecules that may act as antigens, such as proteins or peptides, polysaccharides and, more rarely, other molecules such as nucleic acids.

In the sense used in this description, the expression "therapeutically effective quantity" relates to the quantity of peptides or genetic constructions that enable its expression calculated to produce the desired result and, in general, will be determined, among other causes, by the typical effect of said peptides, sequences and constructions and the therapeutic effect to be achieved. The pharmaceutically acceptable adjuvants and vehicles that may be used in said compositions are the vehicles known by persons skilled in the art. The compositions provided by this invention may be facilitated by any administration route, for which reason said composition will be formulated in the suitable pharmaceutical form for the chosen administration route.

Throughout the description and the claims, the word "comprises" and their variants do not aim to exclude other technical characteristics, additives, components or steps. For persons skilled in the art, other objects, advantages, and characteristics of the invention shall be partly gathered from the description and partly from practice of the invention. The following examples and drawings are provided by way of illustration and do not aim to be limiting of the present invention.

DESCRIPTION OF THE FIGURES

FIG. 2. Expression of the recombinant MSP1a, MSP1b proteins and of the BM95-MSP1a fusion protein in E. coli. The transformed strains of E. coli and the control strain were induced with IPTG and cultivated for 3.5 hours for the expression of recombinant MSP1a, MSP1b and BM95-MSP1a fusion proteins (arrows). The gel was stained with Coomassie brilliant blue and ColorBurst was used as marker of molecular weight in the electrophoresis (Sigma, Aldrich).

EXAMPLES OF EMBODIMENT OF THE INVENTION

Example 1

Construction of the Expression Vector of the a MSP1a Fusion Protein

Plasmid pAF0R1 was constructed to express a mutant protein of MSP1a which does not contain the repeated sequences of amino acids. The msp1α gene which comes from the per1 clone, of the Oklahoma isolate was amplified by PCR. This gene encodes for an MSP1a mutant that lacks six amino acids before the repeated sequences; but which contains the 10 amino acids before the first transmembrane region of the protein. The primers introduced an ATG start codon and the EcoRI and BglII restriction sites for the cloning in phase of the sequence which encodes for the recombinant polypeptide, all in a vector for expression in E. coli.

Figure 1A:
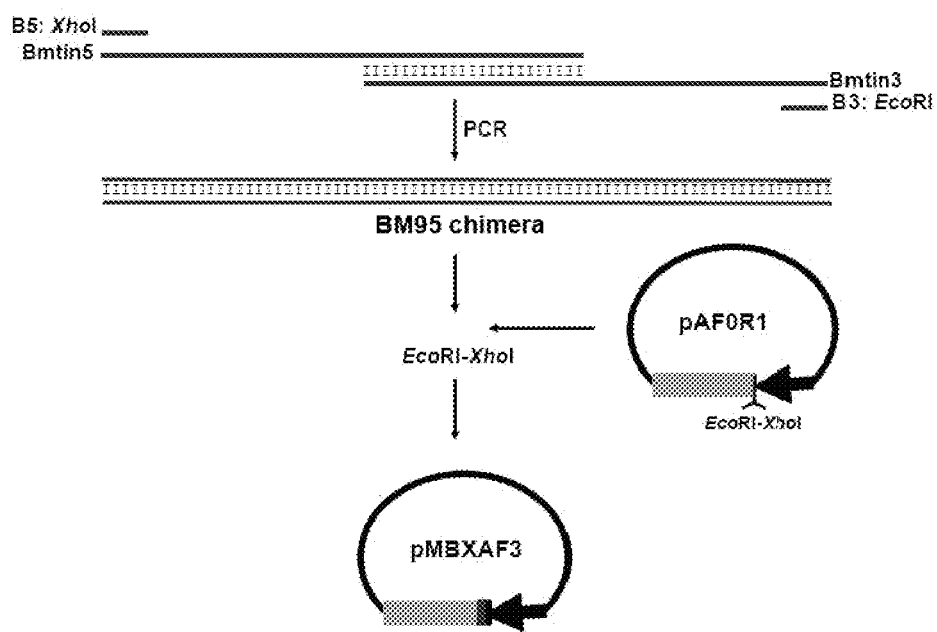
FIG. 1. Construction of the expression vector of the BM95-MSP1a fusion protein (A). Schematic representation of the process used to synthesise the BM95 chimera and fuse it to the MSP1a mutant of A. marginale, which lacks the sequences repeated at the N-terminal end, in the plasmid pAF0R1 (SEQ ID NO: 9) to generate the fusion protein in the expression vector pMBXAF3 (SEQ ID NO: 10). (B) Prediction of the sequence (SEQ ID NO: 11) and structure of the fusion protein MSP1a-BM95 exposed on the E. coli membrane. The sequences of the bm95/BM95 chimera, msp1a/MSP1a and of the plasmid are shown in red, orange and black respectively. It shows the position of the amino acids (aa) of BM95 included in the chimera.

The Bm95 chimera protein was constructed by PCR to give an encoding gene so that the protein had the three immunogenic peptides (SEQ ID NO: 3) which correspond to the sequences of amino acids 21 to 35; 132 to 147 and 397 to 410 of BM95 respectively (SEQ ID NO: 4) (FIGS. 1A and 1B).

First, two oligonucleotides were synthesised, Bmtin5 (SEQ ID NO: 5) and Bmtin3 (SEQ ID NO: 6) and they were hybridised in the central overlapping region (overlapping region Tm=92° C.) (FIG. 1A). Then, a PCR reaction was performed with the oligonucleotides B5 (SEQ ID NO: 7) and B3 (SEQ ID NO: 8) to amplify the Bm95 chimera and introduce an ATG start codon and the sites for the restriction enzymes XhoI and EcoRI for the cloning in the pAF0R1 vector (FIG. 1A).

The PCR reaction was performed using 10 pmol of each primer in a final volume of 50 µl (1.5 mM MgSO4, 1×RT/ Thermus flavus (Tfl) buffer of the avian myeloblastosis virus (AMV), 0.2 mM of each deoxynucleotide triphosphate (dNTP), 5 units of AMV RT, and 5 units of Tfl DNA polymerase) using the RT-PCR Access system (Promega, Madison; Wis., EU). The reactions took place in a Techne automatic thermocycler (model TC-512, Cambridge, England) during 35 cycles. After an initial step of denaturing at 94° C. for 30 seconds, each cycle consisted of a denaturing stage at 94° C. for 30 seconds and a ringing/extension stage of 1 min at 68° C. The products of the PCR were displayed by electrophoresis in 1% agarose gel and the size of the fragments was compared amplified with a band template (1 Kb Plus DNA Ladder, Promega). The product of PCR (amplicon) was purified in resin columns (Wizard, Promega), and it was digested with the enzymes XhoI and EcoRI to clone it in the pAF0R1 vector and generate the pMBXAF3 vector for the expression of the BM95-MSP1a fusion protein (FIG. 1A).

The MSP1a protein contains peptides repeated in the N-terminal region exposed on the surface of A. marginale and which are involved in the interaction of the pathogen with the host cell receptors. The size of the repeated regions of MSP1a varies between 28 and 289 amino acids. These regions are also exposed on the surface of the bacteria when the recombinant protein is expressed in E. coli.

The plasmid pAF0R1 encoding for a mutant of MSP1a which lacks 6 amino acids before the repeated sequences; but which contains 10 amino acids after the first transmembrane region of the putative protein was used as vector for the expression of the peptides of BM95 exposed on the E. coli Surface. The BM95 chimera expressed in this study had 29 amino acids (FIG. 1B), which positions it within the range of sizes of the repeated sequences of MSP1a. Additionally, the tac promoter of the pAR0R1 vector, which is highly inducible, allowed high expression levels of the native MSP1a, mutant MSP1a and MSP1b proteins.

Example 2

Expression and Purification of the BM95-MSP1a Fusion Protein

The plasmids were transformed in the JM109 strain of E. coli for the induction of the expression of the recombinant BM95-MSP1a protein, as occurs with the native MSP1a and MSP1b proteins, used as controls in the experiments. In the constructions, the expressed genes were under the control of the induction promoter tac. The transformed E. coli strains were cultured in LB (Luria-Bertani) medium supplemented with 50 µg/ml of ampicillin and 0.4% (w/v) of glucose, at 37° C. to an optical density of 0.4 uOD600 nm. To induce the expression of the recombinant proteins Isopropyl-β-D-thiogalactoside (IPTG) was added to a final concentration of 0.5 mM and the incubation was continued for 3.5 hours.

To produce the recombinant proteins, the transformed E. coli strains were cultured in 10 ml of LB medium for 2 hours in an orbital stirrer at 37° C. and 200 rpm. Later, the cultures were inoculated in 250 ml of medium, they were incubated in the same conditions for 4 h until reaching 1 uOD600 nm and they were used to inoculate a Biostast Bplus fermenter (B. Braun Biotech, Melsungen, Germany) with 4 L of culture medium. The fermentations were performed at 37° C. and pH 7.0 controlled by addition of 1M HCl or 4M NaOH and at an oxygen concentration dissolved in the medium over 30%, controlled by stirring in a constant air flow of 0.5 l/min. The culture was grown to 0.4 uOD600 nm, IPTG was added to a final concentration of 0.5 mM and the fermentation was continued during a further 3.5 h to induce the expression of the recombinant proteins. The cell growth was monitored throughout the process measuring the optical density at 600 nm.

The cells were harvested by centrifugation at 3,800×g for 10 min at 4° C. and later 1 g samples of the precipitated cells were resuspended in 5 ml of rupture buffer solution (100 mM Tris-HCl pH 7.5, 150 mM NaCl, 1 mM PMSF, 5 mM MgCl2× 6H$_2$O and 0.1% Triton X-100 (v/v)). To break the cells, a Heidolph DIAX 900 sonicator (Bandelin Sonopuls, Berlin, Germany) was used equipped with a titanium microtip, model MS73, 3 mm in diameter and 192 mm in length which was immersed 10 mm in the cell suspension. The frequency of the equipment was fixed at 20 kHz and the noise level at 70 kW. During the rupture, the suspension of cells in 15 ml tubes was kept in an ice bath to prevent overheating. The rupture cycle consisted of intervals of 5 seconds action and 5 seconds rest until completing 10 minutes of total rupture time. After the rupture, the fraction of insoluble proteins associated to the membrane was separated from the soluble proteins by centrifugation at 12,500×g for 15 min at 4° C. and it was stored at −20° C. Later, this fraction was resolved in an electrophoresis gel as described below, and the protein band of interest was extracted from the gel to use it in rabbit immunisation experiments.

The expression levels of the recombinant proteins and the concentrations of proteins during fermentation and in the purification steps were determined using the semiautomatic system for electrophoresis Experion (Bio-Rad, Hercules, Calif., EU). To perform the determinations, 4 µl of the samples were loaded in the Chip Pro 260 (Experion, Bio-Rad) and they were analysed in the Experion following the manufacturer's instructions.

Expression of the recombinant proteins was detected by electrophoresis in 10% polyacrylamide gel (Criterion XT, Bio-Rad). The samples, of 10 μg of total proteins, were applied in each well and the electrophoretic runs were performed at constant current of 20 mA for 4 h. The gels were stained with Coomassie R250 brilliant blue or they were transferred to a PROTRAN BA85 nitrocellulose membrane (Schleicher and Schuell, Dassel, Germany) in a Minie-Genie Electroblotter semi-dry transfer unit (Idea Scientific, Corvallis, Oreg., E.U.) following the manufacturer's instructions, to then be analysed by Western blot.

For the Western blot analysis, the nitrocellulose membranes were blocked with a solution of 5% semi-skimmed milk (w/v) for 1 h at ambient temperature, they were washed three times in tris buffer solution (TBS, 25 mmol/L Tris.HCl, 150 mmol/L NaCl, pH 7.6) and they were incubated for 1 h at ambient temperature with the serum of the rabbits previously immunised with Gavac (Revetmex, Mexico) or with the vaccines which contained the recombinant proteins.

The rabbit antiserum was diluted at concentrations of 1:1000 or 1:5000 respectively in a 3% solution (w/v) of bovine serum albumin (BSA) in TBS buffer solution. Then, the membranes were washed a further three times TBS and they were again incubated with a rabbit anti-IgG polyclonal antibody conjugated with horseradish peroxidise (HRP, Sigma-Aldrich) diluted 1:1000 in TBS. After again washing the membranes the colour was revealed using the 3,3'5,5' tetramethylbenzidine substrate (TMB, Promega, EUA) for 20 minutes.

The live cell immunofluorescence assay, to detect expression of the recombinant BM95-MSP1a fusion protein, was performed by using the polyclonal antibodies against MSP1a, BM86 and the BM95-MSP1a fusion protein produced in rabbits. The recombinant MSP1a and MSP1b proteins expressed in *E. coli* were used as positive and negative controls.

The induced cells of 1 ml culture (approximately 3×108) were separated by centrifugation at 5000×g for 5 min and they were washed with 1 ml of phosphate buffer solution (PBS). They were again collected by centrifugation, they were resuspended in 100 μl of pre-immune or immune rabbit serum and they were incubated for 30 minutes at ambient temperature. After incubation, they were again separated, washed with PBS and resuspended in 100 μl of anti-rabbit goat IgG solution marked with fluorescein (KPL, Inc., Gaithersburg, Md., USA) diluted 1:100 in 3% goat serum (Sigma Aldrich) in PBS. They were again incubated, for 30 minutes at ambient temperature, and the cell-antibodies complex was separated by centrifugation, it was washed with PBS and resuspended in 100 μl of 3% goat serum in PBS. Finally, the cells were spread on glass sheets and air dried, before being fixed in methanol and washed PBS. The dry cell spread was mounted on a slide with Mowiol/glycerol/1,4-diazabicyclo-(2,2,2)-octane (DAPCO, Sigma) and they were examined with an epifluorescence microscope (Eclipse 50i, Nikon Instruments Inc., Melville, N.Y., USA).

With constructed plasmid pMBXAF3, a high expression level of the BM95-MSP1a fusion protein was achieved in *E. coli*. In the fermenter, the BM95-MSP1a fusion protein started to be accumulated after 0.5 h. of induction with IPTG and its final concentration reached 2.8% of the total protein produced by the cells after 3.5 h. of induction (FIGS. 3A and 3B).

Figure 3A:
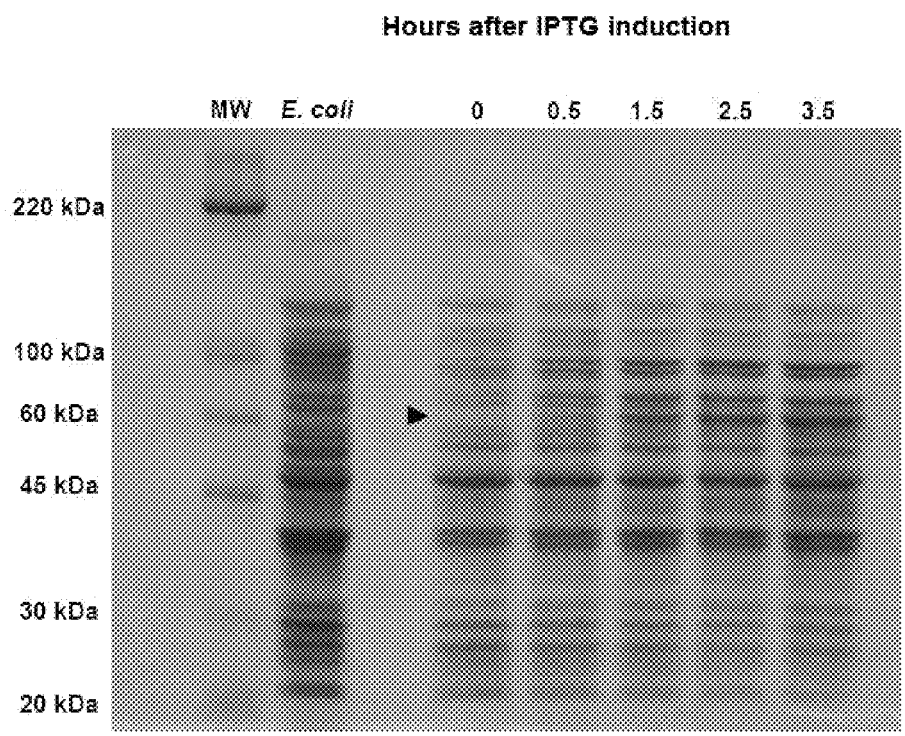
FIG. 3. Expression kinetics of the BM95-MSP1a fusion protein in E. coli. (A) The strains were transformed with the pMBXAF3 vector, cultivated in the fermenter and induced with IPTG for the expression of the BM95-MSP1a fusion protein (arrow). Samples were taken equivalent to 10 μg of total proteins at different times after induction with IPTG and they were run in a 10% polyacrylamide gel. The gel was stained with Coomassie brilliant blue and a strain of transformed E. coli was included only with the vector and induced in the same conditions. The ColorBurst marker (Sigma, Aldrich) was used as standard of molecular weight in the electrophoresis gel. (B) The cell growth was monitored measuring the optical density ($OD_{600nm}$) of the culture during fermentation. The protein concentration was determined via the automated electrophoresis system (Bio-Rad, Hercules, Calif., USA) and the concentration of the proteins of interest was expressed as percent of the total proteins (red line). The moment of induction with IPTG is indicated in the figure.
Figure 3B:
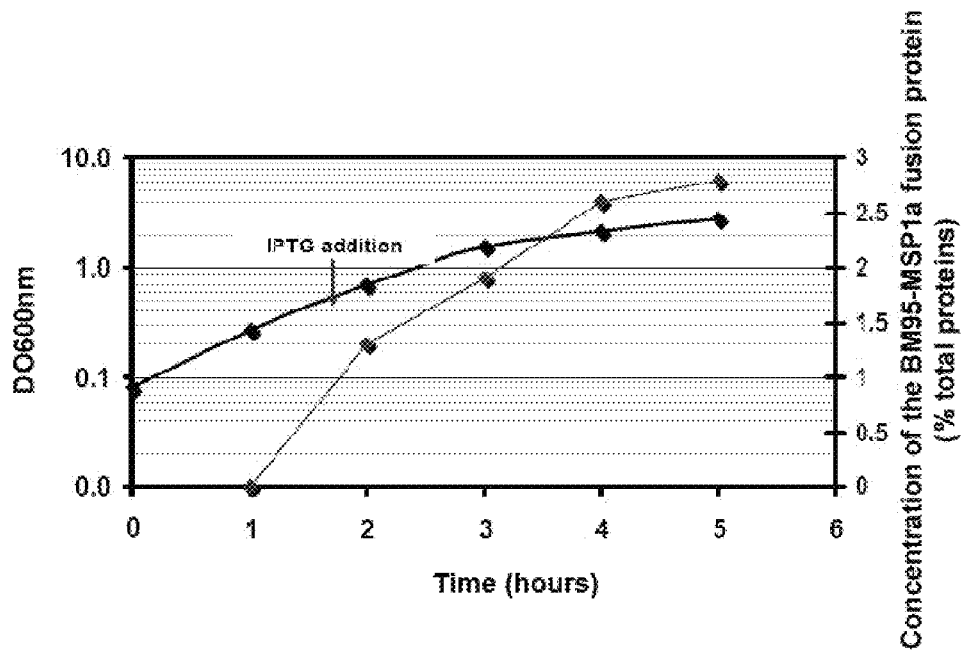

The molecular weight of the BM95-MSP1a fusion protein was estimated between 65 and 70 kDa per SDS-PAGE (FIGS. 2 and 3A). This value was in agreement with the theoretical estimate of 67 kDa, of which 62 kDa correspond to the first 5 amino acids preceding the BM95 chimera protein and the MSP1a region and 5 kDa to the BM95 chimera (FIG. 1B).

Figure 4:
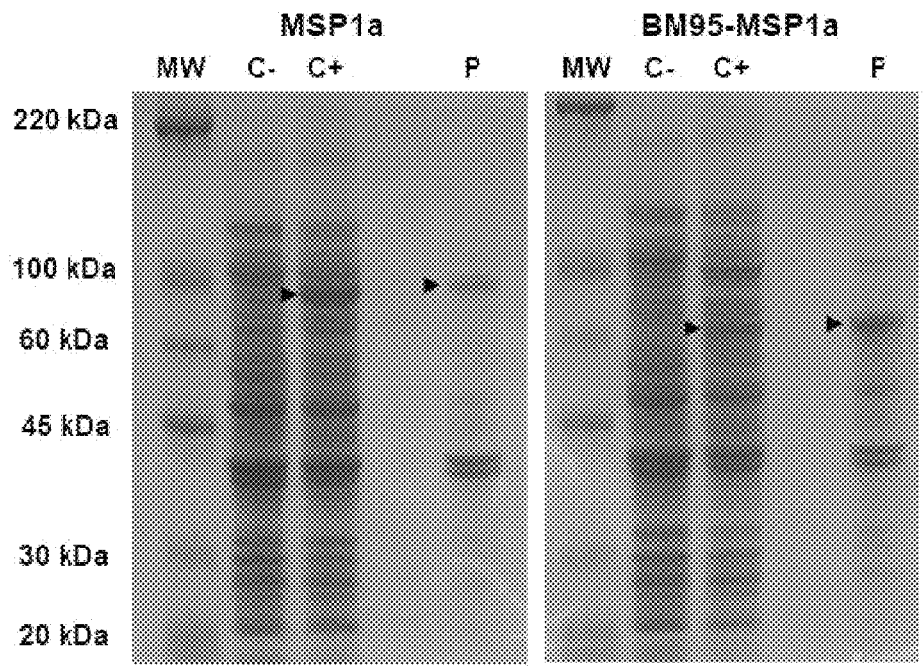
FIG. 4. Location of the recombinant BM95-MSP1a protein in the fraction of insoluble proteins associated to the E. coli membranes. Samples equivalent to 10 μg of total proteins of transformed E. coli only with the vector (C−) or with the expression vectors of MSP1a or BM95-MSP1a (C+), after 3.5 h. of induction were loaded in each well of 10% polyacrylamide gel. The E. coli cells that expressed the recombinant MSP1a and BM95-MSP1a proteins were lysed by sonication and the fractions of soluble and insoluble proteins associated to membranes were separated by centrifugation. 5 μg of total proteins of the insoluble fraction (P) were loaded in the gel wells. The was stained with Coomassie brilliant blue and the ColorBurst standard was used as marker of molecular weight in the electrophoresis (Sigma, Aldrich). The position of the recombinant proteins is indicated with arrows.

An experiment was performed to characterise and purify the BM95-MSP1a fusion protein. The *E. coli* were broken by sonication and the fractions of soluble and insoluble proteins associated to membranes were separated by centrifugation. The result showed that both the BM95-MSP1a fusion protein and the recombinant MSP1a protein were located in the insoluble fraction associated to the membranes and there was no evidence of their accumulation in the cytoplasm (FIG. 4).

Example 3

Immunization of Rabbits and Antiserum Preparation

Three groups of two rabbits of New Zealand race were immunised at weeks 0, 3 and 6 with doses of 1 ml containing 50 μg of the purified MSP1a protein and BM95-MSP1a fusion protein, adjuvated in Montanide ISA 50 V2 (Seppic, Paris, France), and BM86 (Gavac, Revetmex, Mexico). The vaccines were supplied subcutaneously using a tuberculin syringe with 27½ G needle. Two weeks after the last immunisation, blood samples were taken from each rabbit in sterile tubes, they were taken to the laboratory, the sera were obtained by centrifugation and they were later stored at −20° C. The rabbits were kept and cared for in accordance with the Laboratory Animal Use rules.

Figure 5:
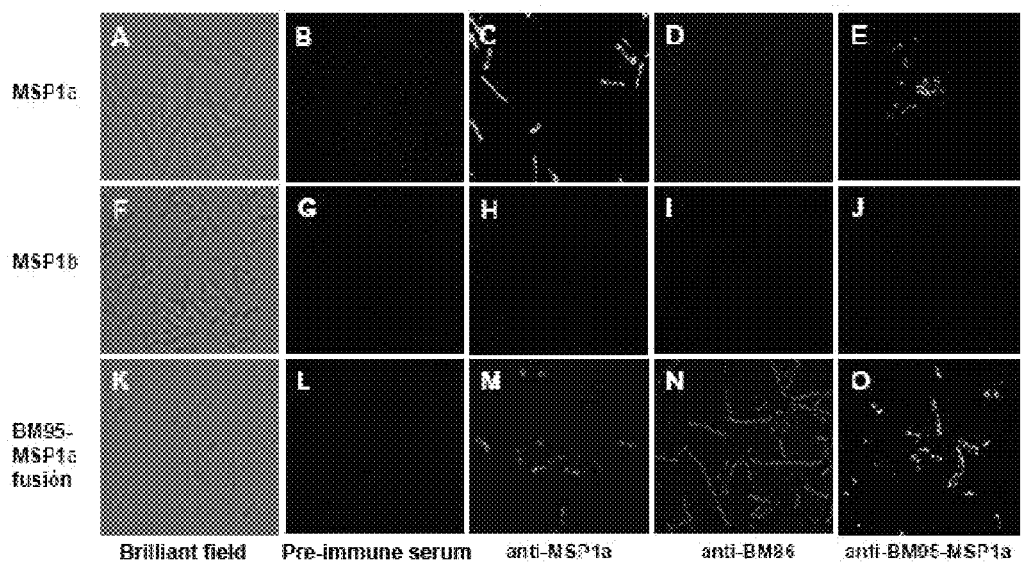
FIG. 5. Exposure of the BM95-MSP1a fusion protein on the E. coli surface. In the immunofluorescence of live cells of the strains of transformed E. coli that expressed the proteins MSP1a (A-E), MSP1b (F-J) and the BM95-MSP1a fusion protein (K-O) they reacted with the primary antibody or the pre-immune serum (B, G, L), MSP1a (C, H, M), BM86 (D, I, N) and BM95-MSP1a (E, J, O), followed by a secondary reaction with a goat antibody directed against rabbit IgG marked with peroxidase (1000× enlargement).

An immunofluorescence assay was performed with live cells (IFA) to analyse if the BM95-MSP1a fusion protein was exposed on the *E. coli* surface (FIG. 5). The expected results were obtained using *E. coli* cells as controls that expressed the recombinant MSP1a and MSP1b proteins and using the pre-immune rabbit sera (FIGS. 5A-L). In addition to this, the IFA of the strain of *E. coli* that expressed the BM95-MSP1a fusion protein showed that the protein was exposed on the cell surface (FIGS. 5K-O).

Figure 6:
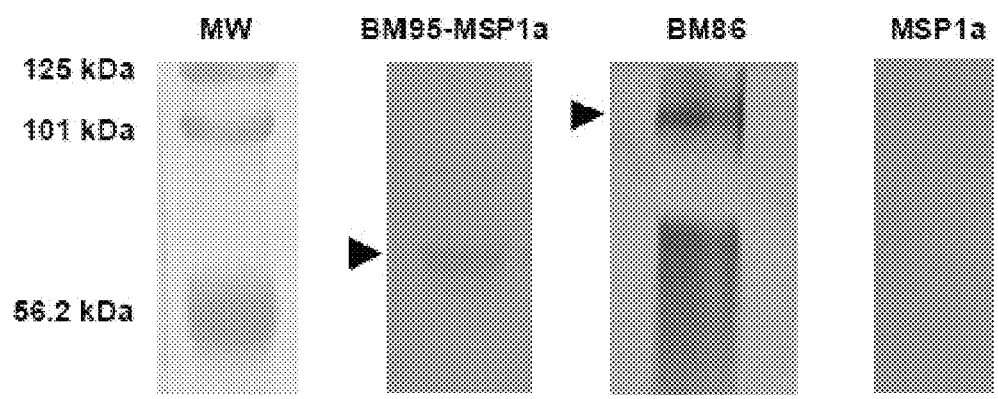
FIG. 6. Recognition of the BM95-MSP1a fusion protein by anti-BM86 antibodies. Samples equivalent to 10 μg of total proteins of E. coli, after 3.5 h of induction with IPTG to express the recombinant MSP1a or BM95-MSP1a proteins, were loaded in each well, in 10% polyacrylamide gel. As positive control, 6 μg of the recombinant BM86 protein were used. For the Western-blot analysis, the proteins were transferred to a nitrocellulose membrane, exposed to rabbit antibodies against BM86 and revealed with the anti-rabbit conjugate coupled to horseradish peroxidase. The position of the fusion protein and BM86 is indicated with arrows. In the protein electrophoresis, the following were used as molecular weight markers: β-galactosidase: 125 kDa; phosphorylase: 101 kDa and bovine serum albumin: 56.2 kDa (BioRad, Richmond, Calif., USA).

The antigenic characterisation of the BM95-MSP1a fusion protein was performed with live cell immunofluorescence. The BM95-MSP1a protein was not only recognised by the specific rabbit antibodies immunised with the fusion protein (FIG. 5O), but also by antibodies against the MSP1a protein (FIG. 5M) and against BM86 (FIG. 5N). Furthermore, the rabbit sera immunised with the recombinant protein recognised the fusion protein by Western-blot (FIG. 6). These results indicated that the epitopes of the fusion protein exposed on the cell surface were recognised by anti-BM86 antibodies and demonstrated that the BM95 epitopes were translated correctly and maintain their antigenicity after fusion.

The invention claimed is:

1. An expression system for expressing at least one peptide on the surface of a bacteria, said peptide comprising:
   a bacterial membrane-binding region and an exposed region, wherein the bacterial membrane-binding region comprises
   the amino acid sequence SEQ ID NO: 1.

2. The expression system of claim 1, wherein the bacteria is *E. coli*.

* * * * *